United States Patent [19]

Fakhrai

[11] Patent Number: 5,088,472

[45] Date of Patent: Feb. 18, 1992

[54] RETRACTOR

[76] Inventor: Mehdi Fakhrai, 1242 S. Barrington Ave., Apt. 201, Los Angeles, Calif. 90025

[21] Appl. No.: 504,260

[22] Filed: Apr. 4, 1990

[51] Int. Cl.⁵ .............................................. A61B 17/02
[52] U.S. Cl. ...................................................... 128/20
[58] Field of Search ............................ 128/20, 17, 18; 269/328

[56] References Cited

U.S. PATENT DOCUMENTS

| | | | |
|---|---|---|---|
| 3,035,582 | 5/1962 | Seiger | 128/20 |
| 3,766,910 | 10/1973 | Lake | 128/20 |
| 4,344,420 | 8/1982 | Forder | 128/20 |
| 4,726,356 | 2/1988 | Santilli et al. | 128/20 |
| 4,813,401 | 3/1989 | Grieshaber | 128/20 |
| 4,852,552 | 8/1989 | Chaux | 128/20 |

Primary Examiner—Theatrice Brown
Assistant Examiner—Mark S. Graham
Attorney, Agent, or Firm—Blakely, Sokoloff, Taylor, Zafman

[57] ABSTRACT

The invention is a sternal retractor comprising a pair of arms with sternum engaging blades thereon and a curved cross bar on which said arms are disposed such that in use the retractor can open the bottom of the sternum more than the top of the sternum to minimize damage and injury to the upper ribs and numbness which sometimes results in the hands of open chest surgery patients. The retractor also has application for other surgical procedures, as well, for the same general purpose of providing an opening of varying size along the length of an incision.

20 Claims, 5 Drawing Sheets

FIGURE 4
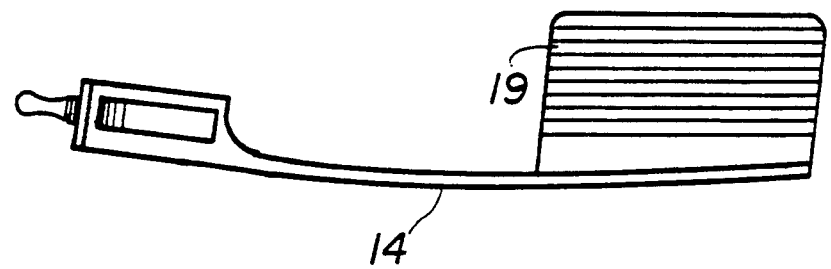
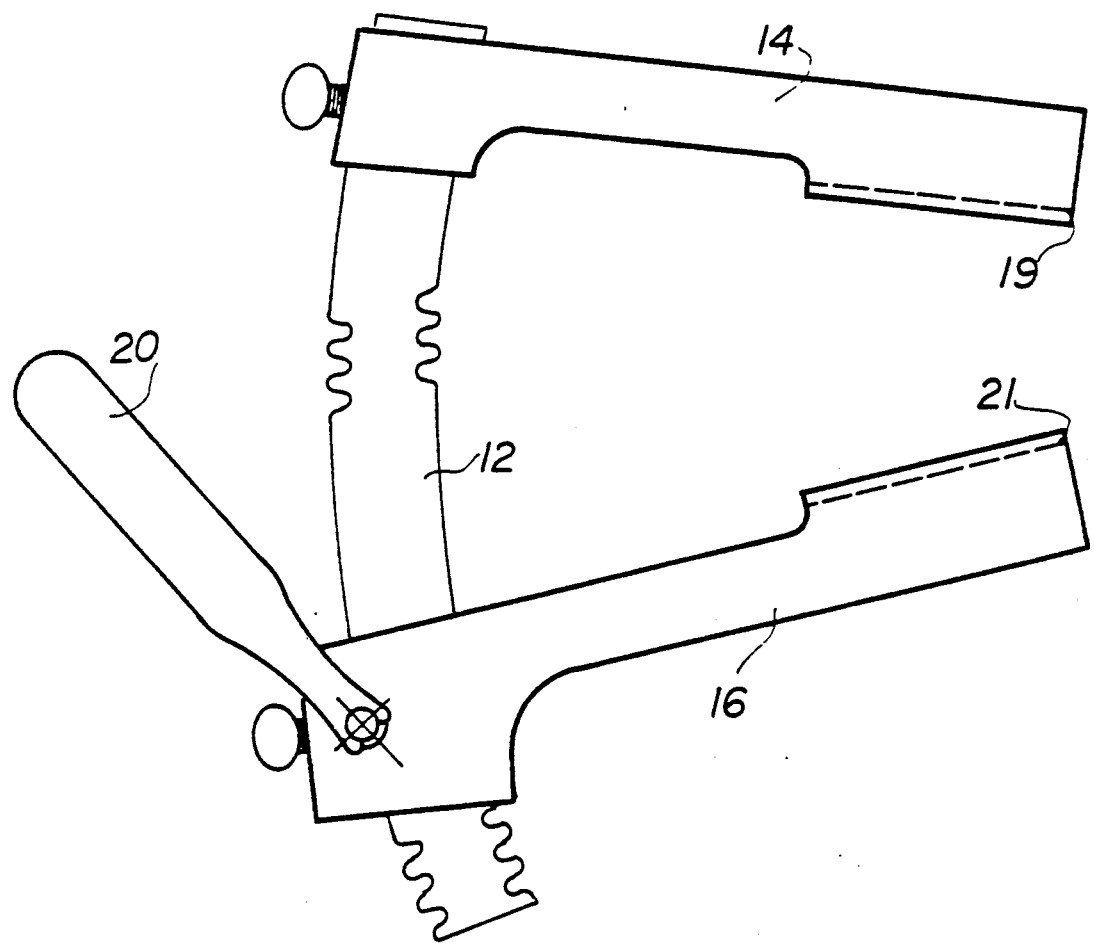
FIGURE 5

RETRACTOR

BACKGROUND OF THE INVENTION

1. Field of the Invention

This invention relates to the field of medical surgical tools, and more particularly, to retractors for chest surgery.

2. Art Background

In open chest surgery, and particularly for cardiac surgery, the sternum is split with a chest saw and is held open by a retractor. The sternum is a short bone in the middle of the chest to which all of the ribs are attached either directly, or indirectly. The ribs attached to the top of the sternum are shorter than the ribs attached to the bottom of the sternum. Accordingly, when the chest is opened using the retractor, more stress is placed on the shorter upper ribs than the longer lower ribs, as explained in more detail below. Such stress causes various problems including broken ribs.

Typical prior art retractors, also termed sternal spreading or chest spreading retractors, comprise two elongated metal members, termed arms, with blades disposed thereon to capture the sternum, the arms being parallel to each other, and a rack or bar with teeth on which the arms are disposed. One of the arms is fixed in position on the rack, and the other arm is equipped with a pinion for moving the other arm along the rack. The prior art retractors opened so that the arms remain parallel with respect to each other throughout their range of motion. Accordingly, in use, the sternum was displaced an equal amount along the entire length of the retractor. Prior art retractors include those devices which have long blades, short blades, multiple short blades or bent arms. Also, for pediatric and small patients, a small sized retractor of the same general configuration as described above may be used.

One recent prior art device comprises a pair of blades which are pivotable through the plane defined by the blades and the bar connecting them. This device is intended to provide pressure evenly along the entire sternum and it opens in a generally triangular configuration as opposed to the generally rectangular configuration. However, the device does not provide positive control of the movement of the sternum as it is opened and does not necessarily open the sternum to a desired position. The device is described in U.S. Pat. No. 4,627,421 issued to Symbas et al.

Another prior art device described in Chaux et al., U.S. Pat. No. 4,852,552 comprises a sternal retractor with blades which rotate in two different axes to permit one portion of the split sternum to be raised above the other portion in order to provide access to particular portions of the chest cavity.

It has been observed that as a result of the use of such prior art devices, that following the surgery, a substantial percentage of patients develop a neuropathy in which numbness occurs in their left or right hand, and specifically, in the fourth and/or fifth digits (the ring finger and little finger). This numbness usually disappears after a while, but it has been known to occur for a substantial period of time, and in any event, such numbness is at best annoying to the surgical patients. The apparent cause of this numbness is that in opening the chest, the opening of the ribs puts substantial pressure on the lower branch of the brachial plexus. The lower ribs are longer and also have more cartilage which permits them to be spread more easily and with less risk than the upper ribs. Also, the lower ribs are not connected to any neurologically important portion of the plexus.

One method of overcoming this problem of applying excessive pressure to the upper ribs and the adjacent portion of the plexus has been for the surgeon to attempt to position the retractor as low as possible so that there is minimal pressure on the upper, shorter ribs. However, this approach is not particularly desirable because the surgeon is not able to position the retractor in the most advantageous position for retraction of the chest. The present invention overcomes the foregoing deficiencies of the prior art devices and methods.

SUMMARY OF THE INVENTION

The present invention is a retractor of the general type found in the prior art with certain improvements therein which eliminate the problem which occurs during cardiac or other open chest surgery wherein numbness of the fourth and fifth digits of the right and/or left hand is caused when the chest is opened and held open with the prior art retractors and methods. The present invention also minimizes the risk of breaking ribs, particularly the shorter ribs, during such surgery.

The present invention comprises a retractor, and specifically a sternal spreader, having two arms with blades disposed on each arm, said arms being disposed on a cross bar, sometimes referred to as a rack. The invention specifically comprises the cross bar being curved rather than straight, as is provided in the prior art. The arms remain generally perpendicular to the cross bar as they are moved along the cross bar closer to and away from each other, but in view of the curvature of the cross bar, one end of the arms is always closer to each other than the other end of the arms.

Preferably, for an adult sternal spreader, when the end of the arms adjacent with the short ribs is approximately 4 inches apart, the end of the arms adjacent the long ribs is approximately 8 inches apart. Also preferably, the curvature of the cross bar is approximately 40°. Of course, the curvature of the cross bar can be varied considerably, the important feature being that the arms spread apart to form a generally triangularly-shaped opening in the chest as the sternum is spread apart. Any form of attachment means for attaching the arms to the cross bar and moving the arms along the cross bar may be employed, the preferred system comprising a rack and pinion.

It is an object of the present invention to provide a retractor which is structurally simple and which does not obstruct the surgeon's view of the chest cavity, and particularly which does creates the largest possible viewing area with a minimal amount of trauma to the ribs.

It is another object of the present invention to provide a retractor which minimizes injury to the brachial plexus during open chest surgery.

It is another object of the present invention to provide a retractor which minimizes the risk of broken ribs, particularly the shorter ribs.

It is another object of the present invention to provide a retractor which can be used in a plurality of configurations with the cross bar being disposed either above or below the surgical area.

It is yet another object of the present invention to provide a retractor which can be provided in a variety of sizes and curvatures and with a variety in the number of blades, as required.

These and other objects of the present invention are achieved by providing a retractor which is shown in several presently preferred embodiments in the drawings which are described briefly below.

BRIEF DESCRIPTION OF THE DRAWINGS

FIG. 4 is a side view of the present invention shown in FIG. 2.

FIG. 5 is a top view of the present invention shown in FIG. 2.

DETAILED DESCRIPTION OF THE INVENTION

Figure 1:
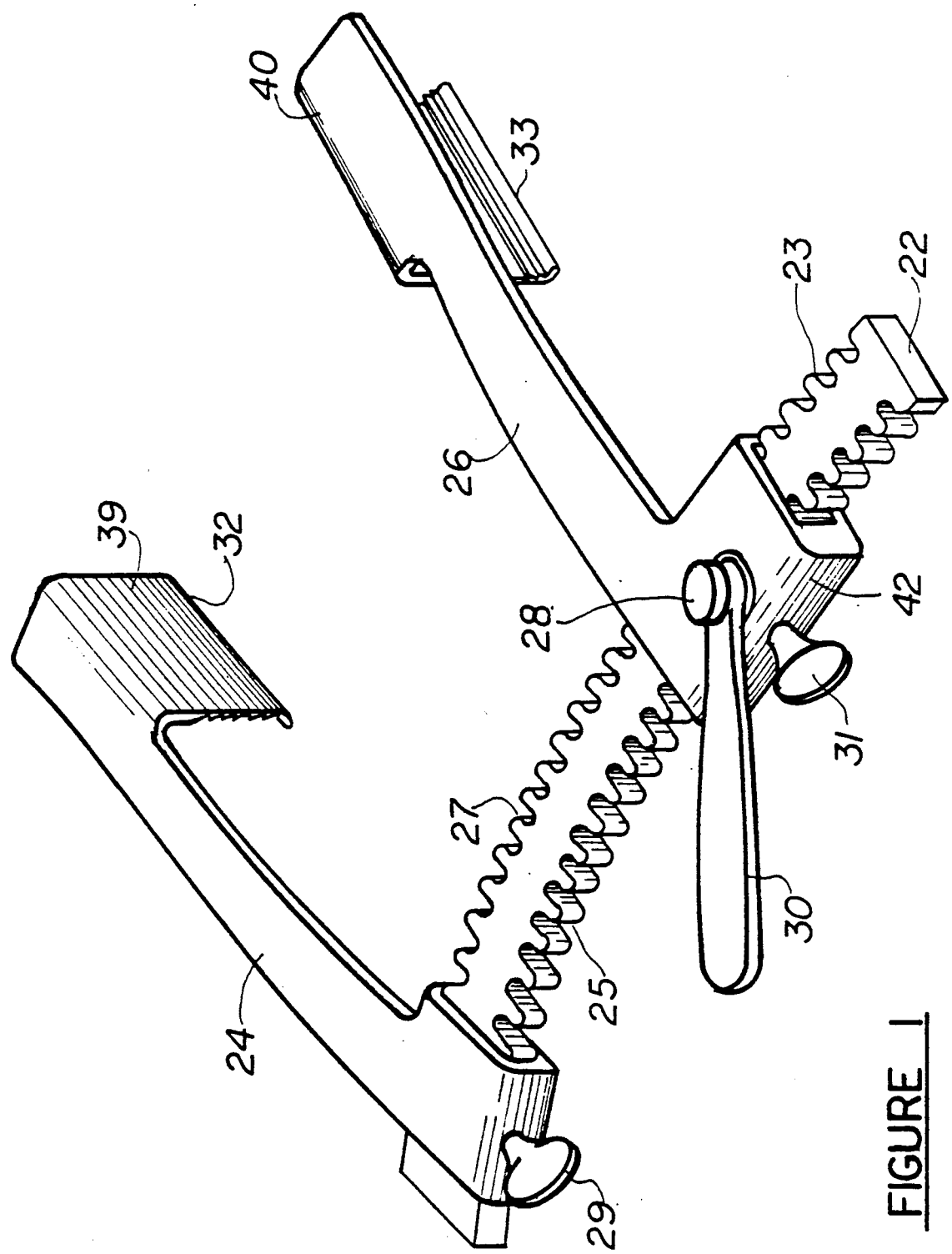
FIG. 1 is a perspective view of the preferred embodiment of the present invention.

As shown in FIGS. 1, 3, 6 and 7, the retractor 23 of the present invention comprises generally a cross bar or rack 22, and a first arm 24 and second arm 26. The cross bar 22 has in the preferred embodiment teeth on two opposing surfaces 25 and 27 for reasons that will be explained below. The critical element of the present invention is that the cross bar 22 is curved so that the arms 24 and 26 are not parallel to each other when the arms are opened or spread apart, but are angled outward away from each other as shown in FIG. 1. When the arms are closed and adjacent each other, they are substantially parallel to each other thereby facilitating the insertion of the blades in an open sternum. One and possibly both arms may be moved along bar 22. Preferably, the moving means comprises a pinion 28 driven by handle 30. This arrangement allows the present invention to be installed and to force the cut portions of the sternum apart. The arms have disposed thereon blades 32 and 33 which are common to prior art chest separators and which are adapted to secure the sternum after it is cut. The present invention includes the use of blades which are longer than those depict as well as multiple blades on a single arm, and angled arm blades, all of which is well known in the art.

In the configuration shown in FIG. 1, the bar 22 would be disposed closer to the head of a patient than the abdomen, so that end 39 of blade 32 and end 40 of blade 23 are further apart than ends 41 and 42. Accordingly, in use, the invented retractor positively forces the sternum into a specific angled position dictated by the curvature of the bar 22 and the distance between the arms. In this way the chest opening can be small at the area adjacent the short ribs and larger at the area adjacent the longer ribs. Thus, while the retractor of FIG. 2, discussed below, is disposed with the bar near the abdomen, the retractor in the configuration of FIG. 1 would be used so that the bar is disposed near the head of the patient. It will be appreciated in this connection that the reversible nature of the preferred embodiment of the present invention is not a requirement of the invention but is the preferred embodiment for purposes of obtaining multiple uses for a single device. The positioning of the bar can be chosen to provide the best view for the surgeon in a manner which is well known in the art.

Figure 2:
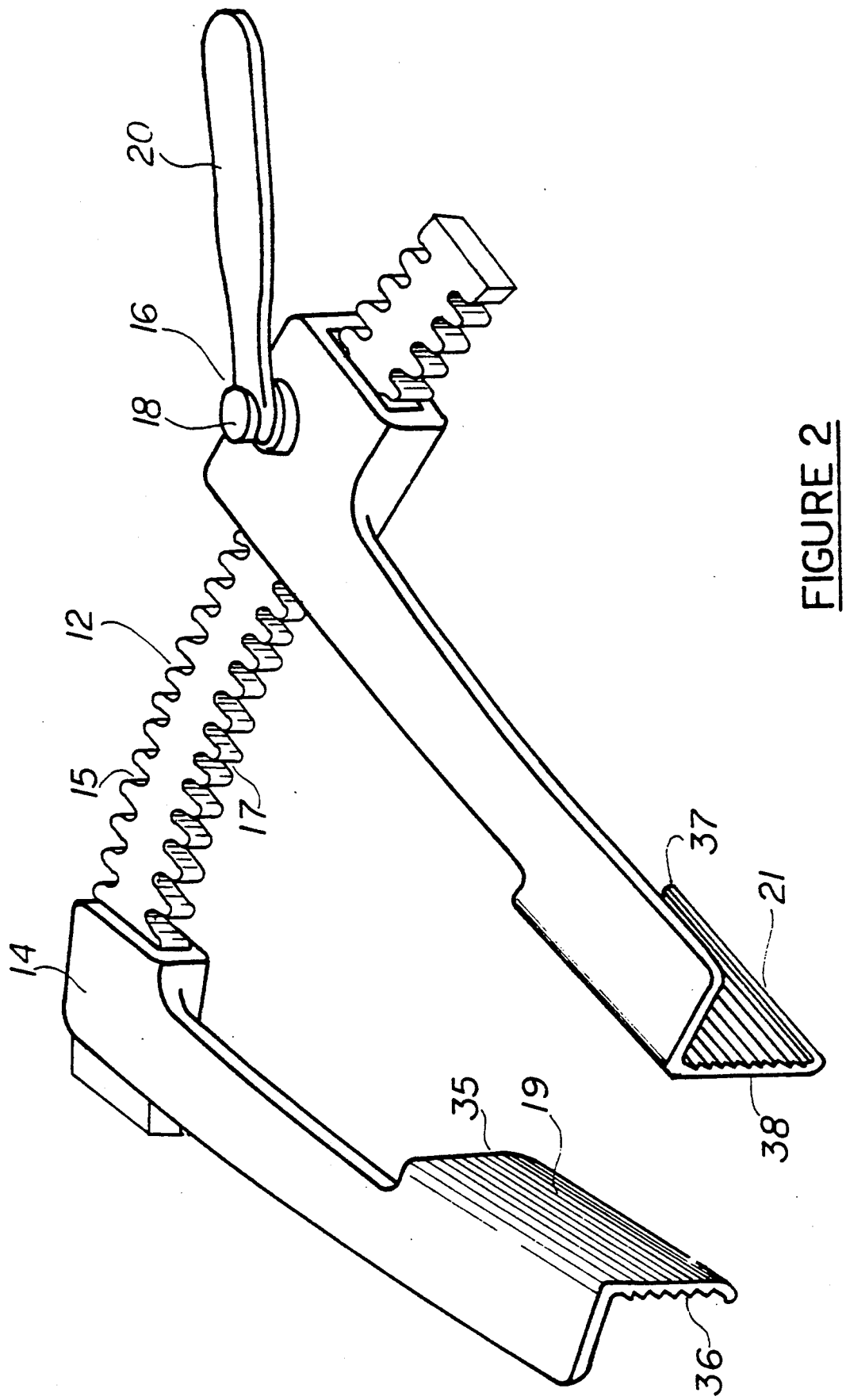
FIG. 2 is another perspective view of the preferred embodiment of the present invention.
Figure 3:
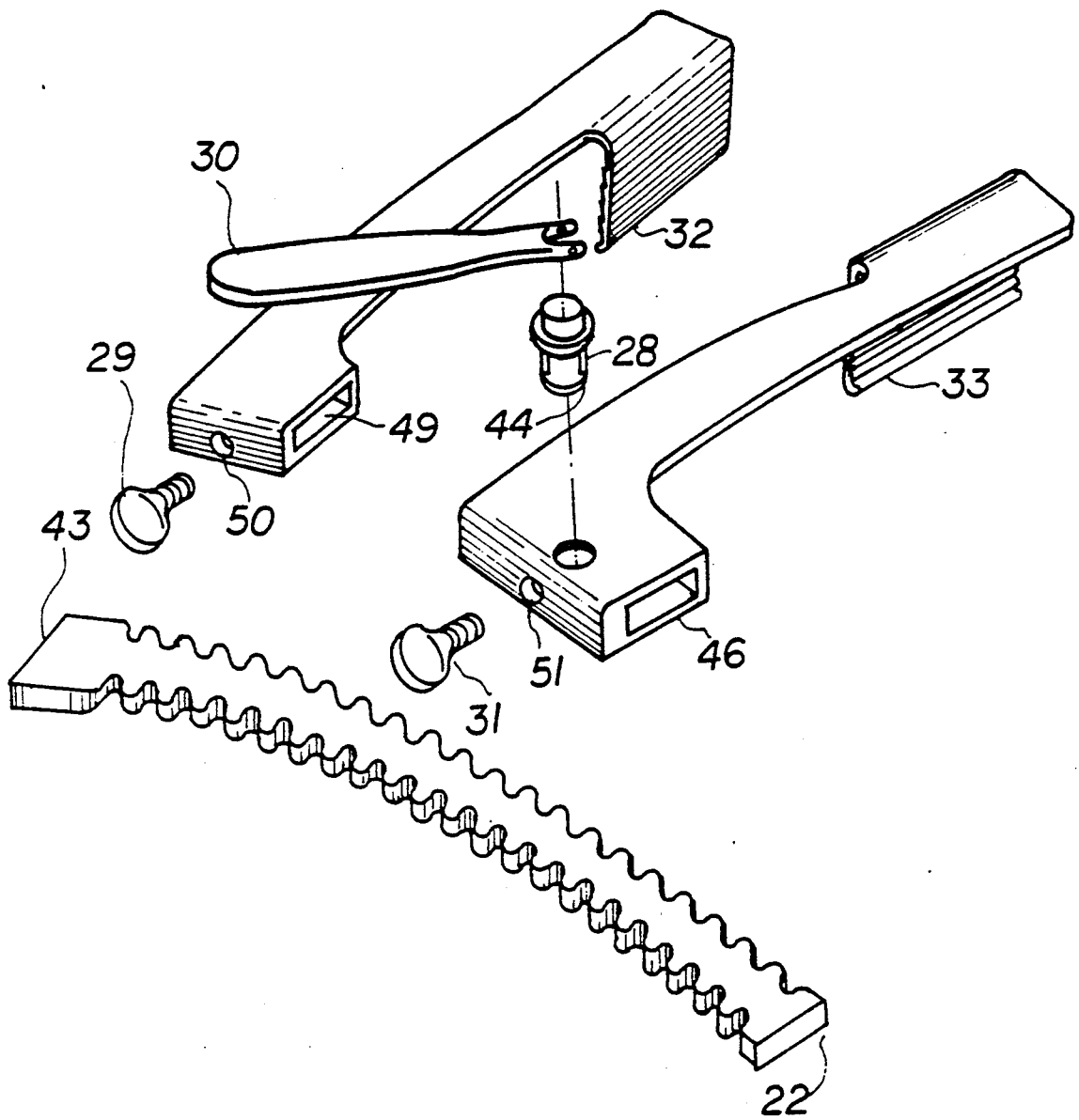
FIG. 3 is a perspective exploded view of the present invention in the configuration shown in FIG. 1.
Figure 6:
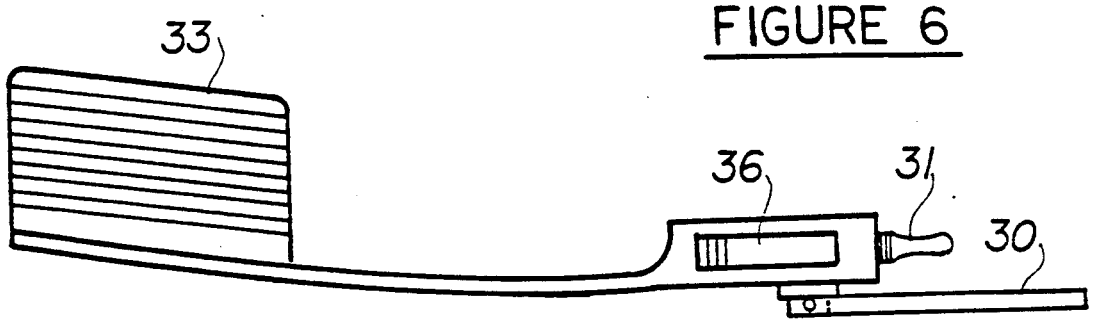
FIG. 6 is a side view of the present invention shown in FIG. 1.
Figure 7:
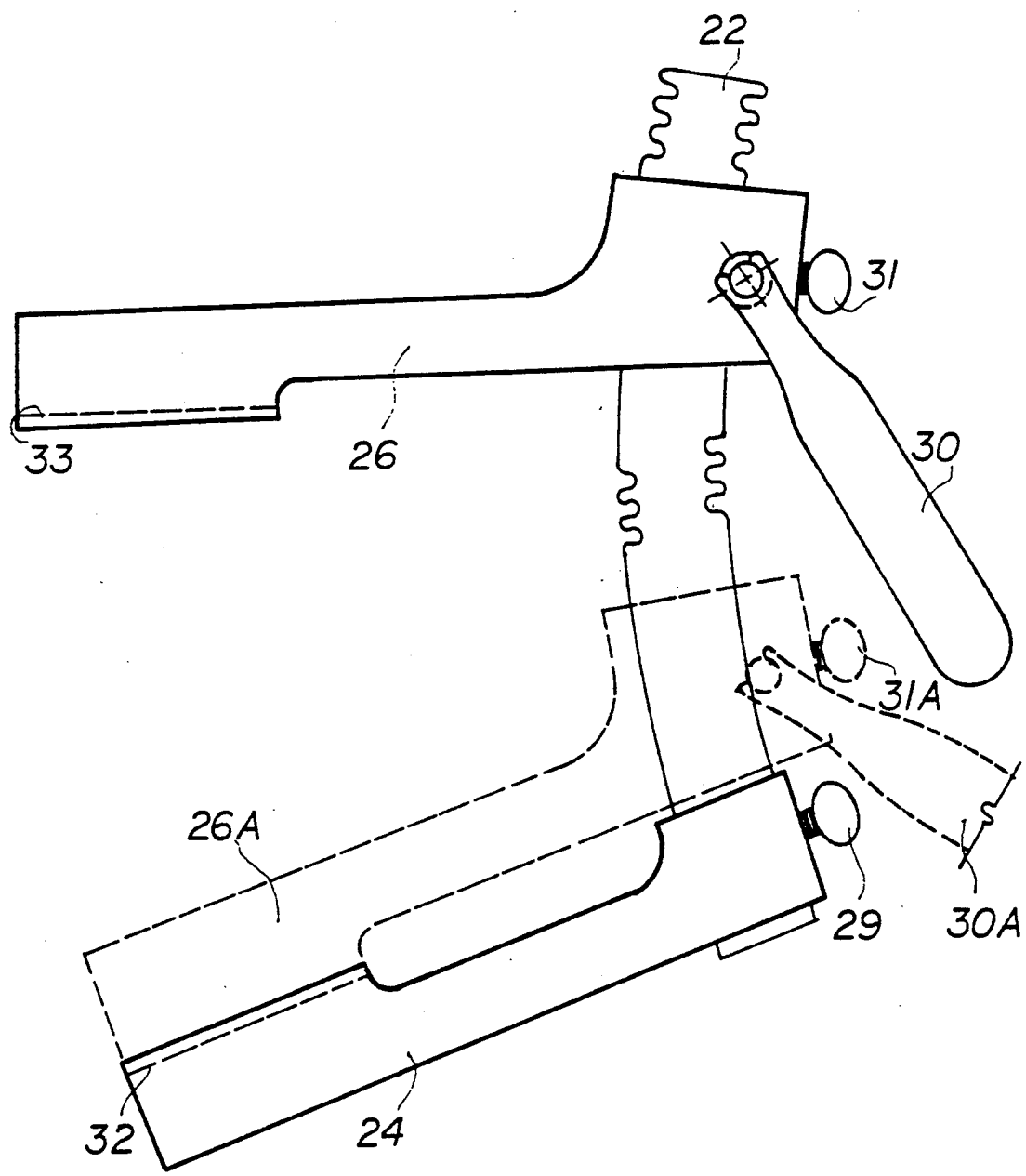
FIG. 7 is a top view of the present invention shown in FIG. 1.

Referring to FIGS. 2, 4, and 5, the retractor 10 of the present invention comprises generally a cross bar or rack 12, and a first arm 14 and second arm 16. The cross bar 12 has in the preferred embodiment teeth on two opposing surfaces 15 and 17 for reasons that will be explained below. The critical element of the present invention is that the cross bar 12 is curved so that the arms 14 and 16 are not parallel to each other when the arms are opened or spread apart, but are angled either outward away from each other as shown in FIG. 1 or inward toward each other as shown in FIG. 2 as described above. When the arms are closed and adjacent each other, they are substantially parallel to each other thereby facilitating the insertion of the blades in an open sternum. One and possibly both arms may be moved along bar 12. Preferably, the moving means comprises a pinion 18 driven by handle 20. This arrangement allows the present invention to be installed and to force the cut portions of the sternum apart. The arms have disposed thereon blades 19 and 21, which are common to prior art chest separators and which are adapted to secure the sternum after it is cut. The present invention includes the use of blades which are longer than those depict as well as multiple blades on a single arm, all of which is well known in the art.

As is further shown in FIGS. 2, 3, 6 and 7, the bar 22 comprises teeth on sides 25 and 27 and the arms 24 and 26 have blades 32 and 33 respectively. Arm 26 has pinion 28 and crank 30, and as shown, has locking pin 31 which screws into hole 50 to secure the arm in the desired position. Arm 24 has locking pin 29 which secures it in place as well by screwing into hole 51 and impinging on the bar 22. Pinion 28 comprises individual teeth 44 adapted to mate with the teeth on bar 22 so that the arm 26 can be cranked open to spread open the chest. The locking pin 29 provides the arm 24 with a means for disconnecting said arm 24 from said bar 22 so that the arms can be reversed if desired to the configuration of FIG. 1, to extend in the direction of the curve of the bar if it is desired to locate the bar above the surgical area rather than below it. Similarly, arm 26 can be removed from bar 22 so that it can be reversed in the configuration of FIG. 1. Bar 22 is provided with a flattened area 43 onto which arm 24 may be secured. Arms 24 and 26 have slots 49 and 46, respectively, in which the bar 22 may be disposed in use.

In the preferred embodiment, the bar is approximately 8 inches long, for adult sternal retractors and has a curvature of 40°. The curvature of the bar may be regular, that is, with a single radius of curvature or it may have multiple radii of curvature along its length to provide variation in the angle of the blades with respect to each other. The curvature of the bar can be of any desired radius, the preferred curvature providing an opening of 8 inches at the bottom of the sternum and an opening of 4 inches at the top of the sternum. The blades can be short, long, multiple or slightly angled to provide the desired secure opening of the sternum.

It will be obvious to a person of ordinary skill in the art that a number of modifications and changes can be made to the subject invention without departing from the spirit and scope of the present invention, which is defined by the claims appended hereto and all equivalents thereof.

I claim:

1. A surgical sternal retractor comprising:

a curved flat rack bar having at least one radius of curvature;

two elongated arms, each of said arms being mounted near one end thereof to said bar in a non-parallel relation to each other and having at least one blade means disposed at the other end thereof; and pinion means for moving at least one of said arms along the bar with sufficient force to spread the sternum.

2. The retractor of claim 1 wherein said curved rack bar comprises teeth on at least one side thereof, and said pinion moving means comprises a pinion associated with at least one arm.

3. The retractor of claim 2 wherein said rack bar comprises teeth disposed on two opposite facing surfaces and wherein said arms may be disposed on said bar in two opposing configurations, one configuration wherein the blades of said arms converge, and one configuration wherein said blades of said arms diverge.

4. The retractor of claim 1 wherein said bar is curved such that in use in open chest surgery, the blades can open the lower portion of the sternum 8 inches while the upper part of the sternum is open 4 inches.

5. The retractor of claim 1 wherein said arms are arranged on said bar in a convergent or divergent arrangement.

6. The retractor of claim 1 wherein said bar has a curvature of approximately 40 degrees.

7. A sternal retractor for use in open chest surgery comprising:

a rack bar having a row of teeth disposed on opposite sides of said bar, said rack bar having a radius of curvature;

a pair of spreader arms connected to said rack bar and extending generally perpendicular to said rack bar in a non-parallel relation to each other, said spreader arms being removable from said rack bar, and one of said spreader arms being movable along said rack bar;

blade means for engaging and spreading split sternal halves comprising sternum engaging retractor blade means attached to each of said spreader arms; and pinion means for moving said movable spreader arm along said rack bar with sufficient force to spread a sternum.

8. The sternal retractor of claim 7 wherein said moving means comprises a pinion disposed in said movable spreader arm, said pinion engaging one of said rows of teeth on said rack bar.

9. The retractor of claim 7 wherein said rack bar is curved such that in use in open chest surgery, the blades can open the lower portion of the sternum 8 inches while the upper part of the sternum is open 4 inches.

10. The retractor of claim 7 wherein said rack bar has a curvature of approximately 40 degrees.

11. A method of opening a sternum and retaining said sternum in an open position for chest surgery comprising:

cutting open the sternum, providing a sternal retractor comprising:

a rack bar having a row of teeth disposed on opposite sides of said bar, said rack bar having a radius of curvature;

a pair of spreader arms connected to said rack bar and extending generally perpendicular to said rack bar, said spreader arms being removable from said rack bar, and one of said spreader arms being movable along said rack bar;

blade means for engaging and spreading split sternal halves comprising sternum engaging retractor blade means attached to each of said spreader arms; and pinion means for moving said movable spreader arm along said rack bar with sufficient force to spread a sternum; whereby said the lower portion of said sternum is spread more than the upper portion of said sternum; and actuating said pinion means for moving said movable spreader arm to spread the sternum a desired amount.

12. The method of claim 11 wherein said rack bar is disposed superior to the sternum and said spreader arms are divergent from said rack bar.

13. The method of claim 11 wherein said rack bar is disposed inferior to the sternum and said spreader arms are convergent from said rack bar.

14. The method of claim 11 wherein said rack bar is curved such that in use in open chest surgery, the blades can open the lower portion of the sternum 8 inches when the upper part of the sternum is open 4 inches.

15. The method of claim 11 wherein said rack bar has a curvature of approximately 40 degrees.

16. A method of opening a sternum and retaining said sternum in an open position for chest surgery comprising:

cutting open the sternum, providing a sternal retractor comprising:

a curved flat rack bar having at least one radius of curvature;

two elongated arms, each of said arms being mounted near one end thereof to said bar in a non-parallel relation to each other and having at least one blade means disposed at the other end thereof; and pinion means for moving at least one of said arms along the bar with sufficient force to spread the sternum.; whereby said the lower portion of said sternum is spread more than the upper portion of said sternum; and actuating said means for moving said movable spreader arm to spread the sternum a desired amount.

17. The method of claim 16 wherein said rack bar is disposed superior to the sternum and said spreader arms are divergent from said rack bar.

18. The method of claim 16 wherein said rack bar is disposed inferior to the sternum and said spreader arms are convergent from said rack bar.

19. The method of claim 16 wherein said rack bar is curved such that in use in open chest surgery, the blades can open the lower portion of the sternum 8 inches when the upper part of the sternum is open 4 inches.

20. The method of claim 16 wherein said rack bar has a single radius of curvature of approximately 40 degrees.

* * * * *